(12) United States Patent
Parker (10) Patent No.: US 8,657,734 B2
(45) Date of Patent: Feb. 25, 2014

(54) IMPLANTABLE UNIVERSAL DOCKING STATION FOR PROSTHETIC HEARING DEVICES

(75) Inventor: John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 525 days.

(21) Appl. No.: 12/935,906

(22) PCT Filed: Mar. 31, 2009

(86) PCT No.: PCT/US2009/038893
§ 371 (c)(1),
(2), (4) Date: Sep. 30, 2010

(87) PCT Pub. No.: WO2010/008630
PCT Pub. Date: Jan. 21, 2010

(65) Prior Publication Data
US 2011/0034755 A1    Feb. 10, 2011

Related U.S. Application Data

(60) Provisional application No. 61/041,185, filed on Mar. 31, 2008.

(51) Int. Cl.
*H04R 25/00* (2006.01)
(52) U.S. Cl.
USPC ............................................................ 600/25
(58) Field of Classification Search
USPC .................................. 600/25; 381/312, 322
See application file for complete search history.

(56) References Cited

U.S. PATENT DOCUMENTS

| 6,039,685 A | 3/2000 | Bushek |
| 6,325,755 B1 | 12/2001 | Bushek et al. |
| 6,482,144 B1 | 11/2002 | Müller |
| 6,786,860 B2 | 9/2004 | Maltan et al. |
| 2002/0032401 A1 | 3/2002 | Fereira et al. |
| 2003/0031336 A1 | 2/2003 | Harrison et al. |

FOREIGN PATENT DOCUMENTS

| WO | WO 01/91678 | 12/2001 |
| WO | WO 2004/024212 | 3/2004 |
| WO | WO 2006/081361 | 8/2006 |
| WO | WO 2009/117767 | 10/2009 |

OTHER PUBLICATIONS

International Search Report for PCT/US2009/038893, filed Mar. 31, 2009, mailed Jun. 11, 2009.
Extended European Search Report, European Application No. 09798353.0, mailed Apr. 5, 2011 (5 pages).
Written Opinion, International Application No. PCT/US2009/038893, mailed Jun. 11, 2009 (6 pages).

*Primary Examiner* — John Lacyk
(74) *Attorney, Agent, or Firm* — Kilpatrick, Townsend & Stockton, LLP.

(57) ABSTRACT

A system for implantation in a recipient comprising: first and second functional implantable components configured to interoperate in order to stimulate the recipient's ear, and an implantable docking station having a plurality of interfaces, the interfaces comprising: a first interface configured to at least one of detachably mechanically and electrically connect to the first component, and at least a second interface configured to at least one of detachably mechanically and electrically connect to the second component, wherein one of the plurality of interfaces is configured to at least one of detachably mechanically and electrically connect to a third component, and wherein the third component is configured to perform an analogous function as one of the first and second components.

24 Claims, 10 Drawing Sheets

IMPLANTABLE UNIVERSAL DOCKING STATION FOR PROSTHETIC HEARING DEVICES

CROSS-REFERENCE TO RELATED APPLICATIONS

The present application PCT/US2009/38893, filed Mar. 31, 2009, and claims the benefit of U.S. Provisional Patent Application 61/041,185; filed Mar. 31, 2008. The contents of these applications are hereby incorporated by reference herein.

BACKGROUND

1. Field of the Invention

The present invention relates generally to prosthetic hearing devices, and more particularly, to an implantable universal docking station for prosthetic hearing devices.

2. Related Art

There are two basic types of hearing loss: sensorineural and conductive hearing loss. Sensorineural hearing loss results from damage to the inner ear or to the nerve pathways from the inner ear to the brain. The majority of human sensorineural hearing loss is caused by abnormalities or damage to the hair cells in the cochlea. Hair cells in the cochlea are the sensory receptors that transduce sound to nerve impulses. Acoustic hearing aids may be appropriate for those who suffer from mild to moderate sensorineural hearing loss. In cases of severe or profound sensorineural hearing loss, a cochlear implant may be the appropriate choice. Cochlear implants bypass the hair cells in the cochlea and directly stimulate the auditory nerve fibers in the cochlea. Stimulation of the auditory nerve fibers creates the sensation of hearing in the recipient.

Conductive hearing loss occurs when there is a problem with the conduction of sound from the external or middle ear to the inner ear. This type of hearing loss may be caused by disease or trauma that interferes with the motion of the ossicles, the three bones of the middle ear that conduct sound to the cochlea. It may also be caused by a failure of the tympanic membrane to vibrate in response to sound channeled from the outer ear through the middle ear. Conductive hearing loss are traditionally treated by acoustic hearing aids and middle ear implants.

Still other individuals suffer from mixed hearing losses, that is, conductive hearing loss in conjunction with sensorineural hearing. In other words, there may be damage in the outer or middle ear and the inner ear (cochlea) or auditory nerve.

While many individuals suffering from conductive hearing loss often use acoustic hearing aids, such hearing aids may not be suitable for certain individuals, such as those suffering from chronic ear infections or from single-sided deafness. An alternative treatment is the use of bone conduction hearing prostheses.

Bone conduction hearing prostheses utilize an individual's bone to transmit acoustic signals to the cochlea. Generally, most bone conduction hearing prostheses function by converting a received sound signal into vibration. This vibration is then transferred to the individual's bone. This skull vibration results in motion of the fluid of the cochlea, thereby stimulating the cochlear hair cells and causing the perception of sound in the recipient.

SUMMARY

In accordance with one aspect of the invention, a system for implantation in a recipient is provided. The system comprises: first and second functional implantable components configured to interoperate in order to stimulate the recipient's ear, and an implantable docking station having a plurality of interfaces, the interfaces comprising: a first interface configured to at least one of detachably mechanically and electrically connect to the first component, and at least a second interface configured to at least one of detachably mechanically and electrically connect to the second component, wherein one of the plurality of interfaces is configured to at least one of detachably mechanically and electrically connect to a third component, and wherein the third component is configured to perform an analogous function as one of the first and second components.

In accordance with another aspect of the invention, a method for upgrading an implanted system comprising an implanted docking station having a plurality of interfaces, a first one of the interfaces at least one of detachably mechanically and electrically connected to a first functional implantable component, and a second one of the interfaces at least one of detachably mechanically and electrically connected to a second implantable component is provided. The method comprises: disconnecting the first component from the implanted docking station, removing the disconnected component from the recipient, at least one of mechanically and electrically connecting a third component having an analogous function as the first component to one of the plurality of mechanical interfaces.

In accordance with yet another aspect of the invention, an implantable docking station is provided. The implantable docking station comprises: a plurality of interfaces comprising: a first interface configured to at least one of detachably mechanically and electrically connect to a first functional implantable component, and at least a second interface configured to at least one of detachably mechanically and electrically connect to a second functional component, wherein the first and second functional implantable components are configured to interoperate in order to stimulate the recipient's ear, and wherein one of the plurality of interfaces is configured to at least one of detachably mechanically and electrically connect to a third component, and wherein the third component is configured to perform an analogous function as one of the first and second components.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to an implantable docking station having a plurality of interfaces which mechanically and/or electrically connect to functional components of an implantable medical device. The plurality of interfaces provides the ability to connect the docking station to a variety of functional components, thereby facilitating the upgrading and/or replacement of prosthesis components.

More specifically, in embodiments of the present invention, the docking station is implantable in the recipient and a first set of functional components are mechanically and/or electrically connected thereto. At a later time, an additional functional component may be connected to the docking station to interoperate with the first set of components. Alternatively, at the later time, one of the first set of components may be replaced by an additional functional component which performs an analogous function as the replaced component. Thus, the docking station provides a surgeon with the ability to upgrade and/or replace components of the implantable medical device without the need to implant mechanical and/or electrical connections specifically suited for the additional component.

As used herein, "analogous components" or components that perform an "analogous" function are those which provide a similar type of benefit to the recipient or the implantable device as compared to the components being upgraded or replaced, but by a different process, or using different anatomy, and so forth. For example, one power source technology may be considered analogous to a newer or better power source technology, since both provide power to the device. Furthermore, an implantable component used to provide hearing stimulation to the recipient by an implanted cochlear array may be considered analogous to an implantable component which provides bone-conduction hearing stimulation, or a middle-ear mechanical stimulator, because both components stimulate a recipient's ear.

Embodiments of the present invention are described herein primarily in connection with one type of implantable medical device, prosthetic hearing devices, and namely Cochlear™ prostheses (commonly referred to as a cochlear prosthetic devices, cochlear implant, cochlear devices, and the like; simply "cochlear implants" herein). It would be appreciated that embodiments of the present invention may be implemented in connection with any implantable medical device now known or later developed. Implantable medical devices envisaged by the present invention include, but are not limited to, cardiac monitors and defibrillators; glucose meters; implantable drug pumps; neural stimulators, including vision and hearing prostheses such auditory brain stimulators, or other devices that electrically, acoustically or mechanically stimulate components of the recipient's outer, middle or inner ear.

Figure 1:
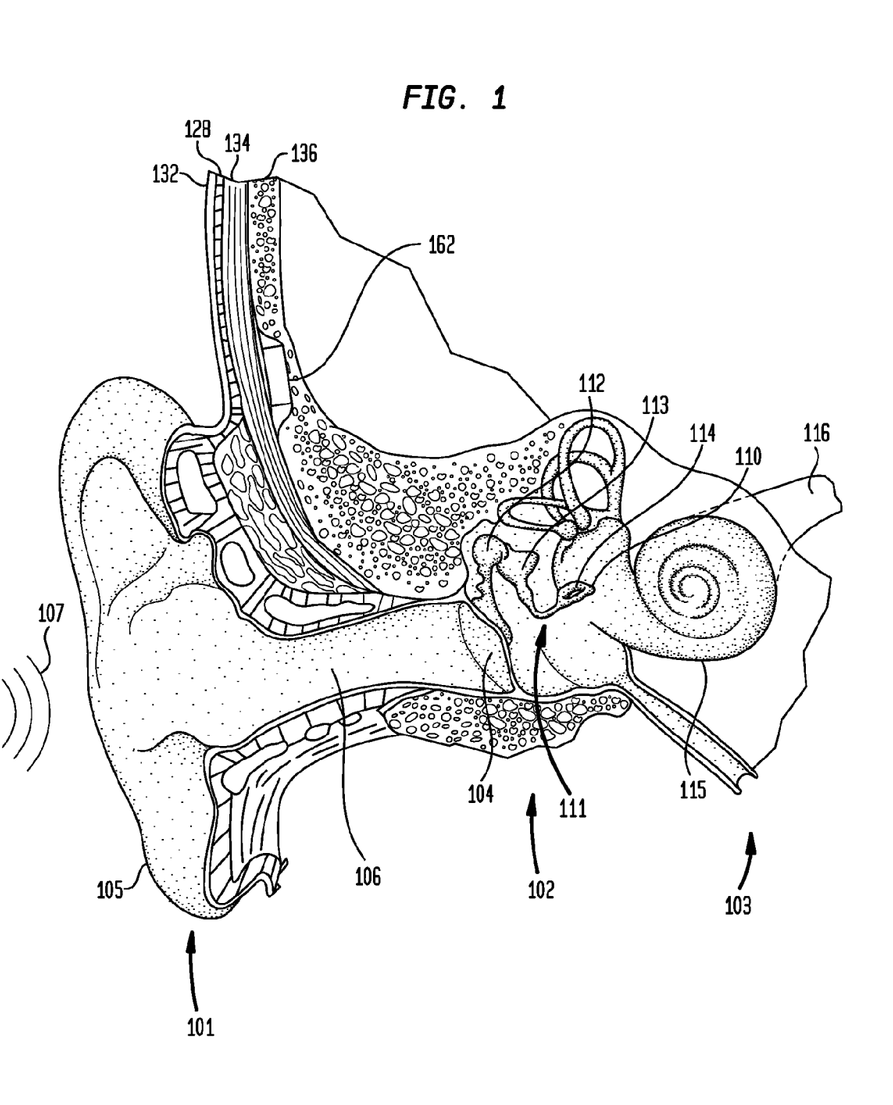
FIG. 1 is a perspective view of embodiments of an implantable a universal docking station for a prosthetic hearing device (not shown) in which embodiments of the present invention may be advantageously implemented.

FIG. 1 is a perspective view of embodiments of an implantable universal docking station 162 for a prosthetic hearing device (not shown) in which embodiments of the present invention may be advantageously implemented. As shown, universal docking station 162 is implanted in the recipient's body. In certain embodiments, the universal docking station 162 is implanted near the recipient's hearing organs. In other embodiments, the proximity to the recipient's organ whose function is being supplemented or replaced is not important and other considerations such as comfort for the recipient, surgical access, long-term wear, and others are factored in the placement of universal docking station 162. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, which includes the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 also illustrates the positioning of one embodiment of the present invention implantable universal docking station 162 relative to outer ear 101, middle ear 102 and inner ear 103 of a recipient of device 162. As shown, universal docking station 162 is implanted within the recipient. As described below, universal docking station 162 is fixed to, or embedded within, bone 136 under muscle 134, fat 128 and skin 132 such that universal docking station 162 is securely fixed to the recipient's bone. In certain embodiments of the present invention, universal docking station 162 is secured to the recipient's bone at the time of the implantation surgery. In other embodiments, universal docking station 162 is configured to integrate with the recipient's bone or tissue over a period of time, for example during the healing or integration process. In still further embodiments, the recipient's bone location where universal docking station 162 is to be implanted is modified surgically to prepare a bed (not shown) or depression into which universal docking station 162 is placed during implantation surgery. This bed is prepared having a height approximately equal to the height of universal docking station 162 such that the entire universal docking station 162 will fit into the bed during the implantation surgery. In other embodiments of the present invention, the height of the bed or depression is greater than the height of universal docking station 162 in order to allow room for additional components in addition to universal docking station 162. In yet further embodiments, the height of universal docking station 162 is configured to be less than the height of universal docking station 162, such that universal docking station 162 is partially received into the bed, but where the partial insertion into the bed is sufficient to retain universal docking station 162 in place. Other combinations of the bed, including the combination of other securing mechanisms or schemes will be apparent to those having ordinary skill in the art, and are considered a part of this invention.

Embodiments of the present invention are generally directed to an implantable universal docking station 162 is secured to the recipient's bone at the time of the implantation surgery. In other embodiments, universal docking station 162 is configured to integrate with the recipient's bone or tissue over a period of time, for example during the healing or integration process. In still further embodiments, the recipient's bone location where universal docking station 162 is to be implanted is modified surgically to prepare a bed (not shown) or depression into which universal docking station 162 is placed during implantation surgery. This bed is prepared having a height approximately equal to the height of universal docking station 162 such that the entire universal docking station 162 will fit into the bed during the implantation surgery. In other embodiments of the present invention, the height of the bed or depression is greater than the height of universal docking station 162 in order to allow room for additional components in addition to universal docking station 162. In yet further embodiments, the height of universal docking station 162 is configured to be less than the height of universal docking station 162, such that universal docking station 162 is partially received into the bed, but where the partial insertion into the bed is sufficient to retain universal docking station 162 in place. Other combinations of the bed, including the combination of other securing mechanisms or schemes will be apparent to those having ordinary skill in the art, and are considered a part of this invention.

Embodiments of the present invention are generally directed to an implantable universal docking station 162 for providing a platform onto which various implantable components of the prosthetic hearing device are coupled. In one embodiment of the present invention, the docking station is surgically secured to a recipient's bone 136. In other embodiments, docking station 162 is implanted inside the recipient but not surgically secured to the recipient's bone. In such embodiments, docking station 162 is secured within the recipient, although not fixed to the recipient's bone. In yet further embodiments, docking station 162 is implanted within the recipient's bone and allowed to integrate with the recipient's bone 136 over time, for example by osseointegration. According to embodiments of the present invention, one or more of the implantable components that are coupled to universal docking station 162 are removable or replaceable without having to move or replace other implanted components. This allows for the replacement of certain implanted components without the risk of injury to the recipient's organs or tissue which may have grown on or into the implanted components which would otherwise be moved from its implanted position. For example, after a cochlear electrode array 246 (FIG. 2A) is implanted into the recipient's cochlea 239 (FIG. 2), electrode array 246 may be in a state of contact with hair cells inside cochlea 239, such that those hair cells may become damaged if the array 246 is moved. According to embodiments of the present invention, the proximal end of the cochlear electrode array is disconnected from universal docking station 162, and the docking station itself along with other implantable component is moved away from the stationary electrode array to be serviced or replaced.

According to certain embodiments of the present invention, universal docking station 162 is a platform that provides only physical support or stability to the implantable components coupled to it. In such embodiments, docking station 162 is connected physically or mechanically to one or more implantable components, via a plurality of interfaces, and does not provide electrical connectivity to those implantable components. In other embodiments, universal docking station 162 has one or more connectors such that an implantable component is connected electrically to docking station 162 to interoperate in order to provide a therapeutic or other benefit to the recipient. In certain embodiments of the present invention, all components of the prosthetic hearing device are implanted within the recipient in what may be referred to as a totally implantable system. In such embodiments, a subset of the implantable components are connected to docking station 162, while in other embodiments, all of the implantable components are coupled to docking station 162.

In other embodiments, one or more of the plurality of interfaces on docking station 162 are electrical in addition to mechanical interfaces, such that the one or more prosthetic hearing device components connected to docking station 162 transmits or receives various signals via docking station 162. In certain embodiments, such interfaces in docking station 162 are simple pass-through or bypass connectors which directly receive signals at one end of a particular conductor and deliver signals to the opposite end of the particular conductor. In other embodiments of the present invention, docking station 162 itself comprises various processors or other circuitry which are configured to receive and process signals, or generate its own signals, for delivery to one or more components of the prosthetic hearing device connected to docking station 162.

In yet further embodiments of the present invention, docking station 162 comprises a plurality of interfaces, some of which are purely mechanical while others are both mechanical and electrical interfaces.

In embodiments of the present invention, docking station 162 may have various implantable components connected thereto. In certain embodiments, the implantable components are one or more stimulating prostheses, including a stimulating prosthetic hearing implant. An example of one stimulating prosthetic hearing implant includes an auditory brain stimulator and cochlear implant (also commonly referred to as cochlear implant devices, cochlear prostheses, and the like; simply "cochlear implant" herein). Other embodiments of the present invention may have other types of stimulating prosthesis, including middle-ear mechanical stimulators, bone conduction transducers, and others.

Figure 2A:
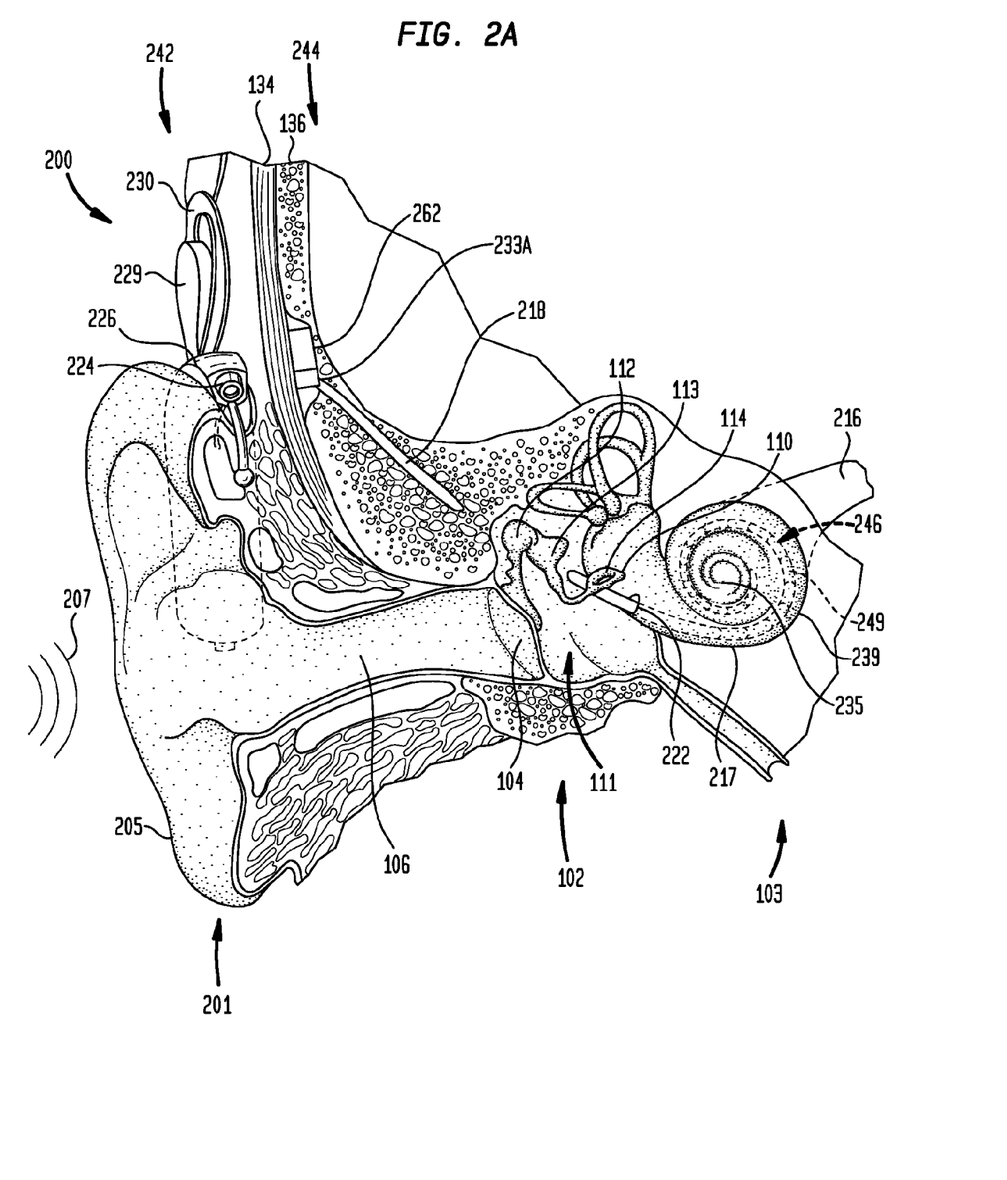
FIG. 2A is a perspective view of one embodiment of a cochlear implant in which embodiments of the present invention may be implemented.

FIG. 2A is a perspective view of one embodiment of a cochlear implant 200 in which embodiments of the present invention may be implemented. Cochlear implant 200 comprises external component assembly 242 which is directly or indirectly attached to the body of the recipient, and an internal component assembly 244 which is temporarily or permanently implanted in the recipient. External assembly 242 typically comprises microphone 224 for detecting sound, a speech processing unit 226, a power source (not shown), and an external transmitter unit 229. External transmitter unit 229 comprises an external coil 230 and, preferably, a magnet (not shown) secured directly or indirectly to external coil 230. Speech processing unit 226 processes the output of microphone 224 that is positioned, in the depicted embodiment, by auricle 205 of the recipient. Speech processing unit 226 generates coded signals, referred to herein as a stimulation data signals, which are provided to external transmitter unit 229 via a cable (not shown).

Internal assembly 244 comprises an internal receiver unit 233A having a stimulator unit (not shown), and an elongate electrode carrier 218. Internal receiver unit 233A comprises an internal transcutaneous transfer coil (not shown), and preferably, a magnet (also not shown) fixed relative to the internal coil. Internal receiver unit 233A is hermetically sealed within a biocompatible housing. The internal coil receives power and stimulation data from external coil 230, as noted above. Elongate electrode carrier 218 has a proximal end connected to the stimulator unit (not shown) of internal assembly 233A and extends from the stimulator unit to cochlea 239. A distal end of electrode carrier 218 is implanted into cochlea 239 via a cochleostomy 222.

Electrode carrier 218 comprises an electrode array 246 disposed at the distal end thereof. Electrode array 246 comprises a plurality of longitudinally-aligned electrodes or electrodes 249. Stimulation signals generated by the stimulator unit are applied by electrodes 249 to cochlea 239, thereby stimulating auditory nerve 216.

In one embodiment, external coil 230 transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, internal receiver unit 233A may be positioned in a recess of the temporal bone adjacent auricle 201 of the recipient.

There are several speech coding strategies that may be implemented by speech processor 226 to convert sound 207 into an electrical stimulation signal. Embodiments of the present invention may be used in combination with any speech strategy now or later developed, including but not limited to Continuous Interleaved Sampling (CIS), Spectral PEAK Extraction (SPEAK), Advanced Combination Encoders (ACE), Simultaneous Analog Stimulation (SAS), MPS, Paired Pulsatile Sampler (PPS), Quadruple Pulsatile Sampler (QPS), Hybrid Analog Pulsatile (HAPs), n-of-m and HiRes™, developed by Advanced Bionics. SPEAK is a low rate strategy that may operate within the 250-500 Hz range. ACE is a combination of CIS and SPEAK. Examples of such speech strategies are described in U.S. Pat. No. 5,271,397, the entire contents and disclosures of which is hereby incorporated by reference. Embodiments of the present invention may also be used with other speech coding strategies, such as a low rate strategy called Spread of Excitation which is described in U.S. Provisional No. 60/557,675 entitled, "Spread Excitation and MP3 coding Number from Compass UE" filed on Mar. 31, 2004, U.S. Provisional No. 60/616,216 entitled, "Spread of Excitation And Compressed Audible Speech Coding" filed on Oct. 7, 2004, and PCT Application WO 02/17679A1, entitled "Power Efficient Electrical Stimulation," which are hereby incorporated by reference herein.

Embodiments of cochlear implant 200 may locally store several speech strategies, such as in the form of a software program or otherwise, any one of which may be selected depending, for example, on the aural environment. For example, a recipient may choose one strategy for a low noise environment, like a conversation in an enclosed room, and second strategy for a high noise environment, like on a public street. The programmed speech strategies may be different versions of the same speech strategy, each programmed with different parameters or settings.

The successful operation of cochlear implant 200 depends in part on its ability to convey pitch information. Differing pitch percepts may be produced by cochlear implant 200 in two distinct ways. First, electrical stimulation at different sites in cochlea 239 excites different groups of neurons and because of the tonotopic arrangement of neurons in cochlea 239, different pitch sensations result. The term "tonotopic" is meant that the percept corresponding to a particular site in the cochlea changes in pitch from lower to higher as the site is changed in an apical 235 to basal 217 direction. Pitch varied in this way is known as "place pitch." Secondly different pulse rates of electrical stimulation produce different pitch sensations. Pitch varied in this way is known as "rate pitch."

Figure 2B:
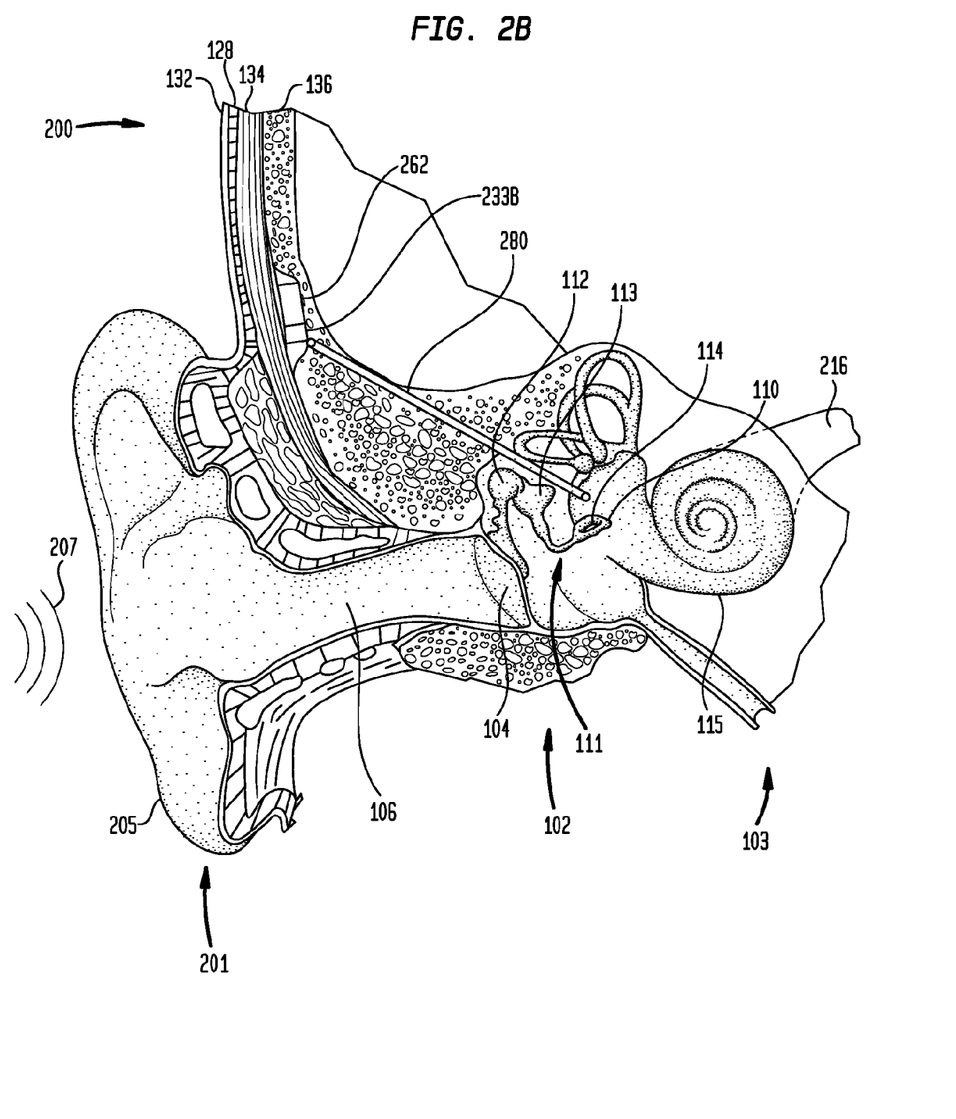
In FIG. 2B, another embodiment of the present invention is shown in which a middle-ear mechanical stimulator is mechanically coupled to a docking station.

In FIG. 2B, another embodiment of the present invention is shown in which a middle-ear mechanical stimulator 233B is mechanically coupled to docking station 262. A communication arm 280 is mechanically coupled to mechanical stimulator 233B so as to transmit mechanical vibration generated by mechanical stimulator 233B through communication arm 280 to one or more anatomy in the recipient that will in turn produce auditory stimulation for the recipient. The vibration generated by mechanical stimulator 233B represents sound 207 after it is processed so as to provide hearing of that sound for the recipient. In the exemplary embodiment illustrated, communication arm 280 is shown, in simplified form, as extending to the recipient's mastoid. By communicating the vibration from mechanical stimulator 233B to the recipient's mastoid, the cochlea can be vibrated and the fluids contained therein moved so as to cause hearing sensation in the auditory nerve.

Figure 3:
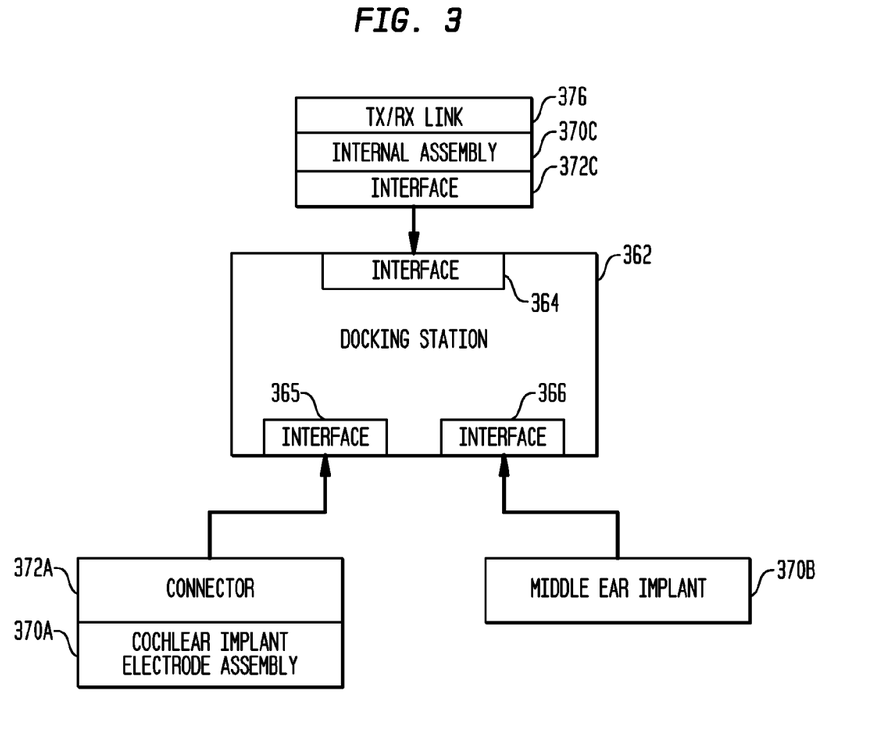
FIG. 3 is a detailed functional block diagram of the implantable a universal docking station.

FIG. 3 is a detailed functional block diagram of the implantable universal docking station 362. In one embodiment of the present invention, a transmitter and receiver link 376 is communicably coupled to one or more external components so as to receive data or power or other signals therefrom. In one particular embodiment of the present invention, receiver unit 370C receives signals from an external component (not shown) for processing and/or delivery to the recipient's auditory system. In the embodiment shown in FIG. 3, connector 372C is configured to connect to a mechanical interface 364 disposed on docking station 362. As illustrated, docking station 362 comprises a plurality of mechanical interfaces 364, 365, and 366. In addition to receiver unit, the embodiment illustrated in FIG. 3 also has a cochlear implant electrode assembly 370A connecting via a electrode assembly connector 372A to mechanical interface 365. A middle-ear mechanical stimulator 370B is also shown in FIG. 3 as connecting to interface 366. It will be appreciated that embodiments of the present invention permit an upgrade path by which components can be individually or separately replaced. That is, when replacement components that generally perform the same function but which provide enhanced or improved performance, quality, longevity and other improvements become available, the upgrade component can be installed in the recipient after the existing component to be replaced is removed. Furthermore, analogous components may replace or may be installed in addition to existing implantable component or components.

After the prosthetic hearing device of the present invention has been implanted within the recipient, and after the device has been in operational mode for some time, due to worn components, defective or malfunctioning components, technological advances, or for other reasons, one may wish to replace or remove one or more of implanted components 370A, 370B or 370C. However, because moving the implanted components in order to replace one of those components may cause damage to the recipient's existing hearing by tearing tissue attached thereto, it would be a great benefit to be able to remove or otherwise move only those components which need to be moved in order to execute the replacement. According to embodiments of the present invention, a surgeon may, for example, remove only internal component 370A or 370B or 370C for repair or replacement.

In other embodiments of the present invention, docking station 362 may also comprise various electronic circuits and processors and docking station 262 may need to be replaced. In such embodiments, universal docking station 362 is disconnected or otherwise de-coupled from the various components not needed to be replaced or removed, exchanged for a different universal docking station 362, and then reconnected to the various components already in place inside the recipient. For instance, in one embodiment, in its operational condition universal docking station 362 is coupled to an electrode array 370B, the distal end of which is already positioned within the recipient. Connector 372B is disconnected from connector interface 364 on universal docking station 362, and universal docking station 362 is removed from within the recipient's body. After a new universal docking station 362 is inserted into the recipient's body, connector interface 364 is connected with the connector 372B, and the prosthetic hearing device is returned to operational mode, either immediately or after some healing time has passed. It is to be understood that universal docking station 362 may comprise one or multiple connector interfaces 364, and that the connector interfaces 364 may differ from one another, as will be described in further detail below.

Figure 4:
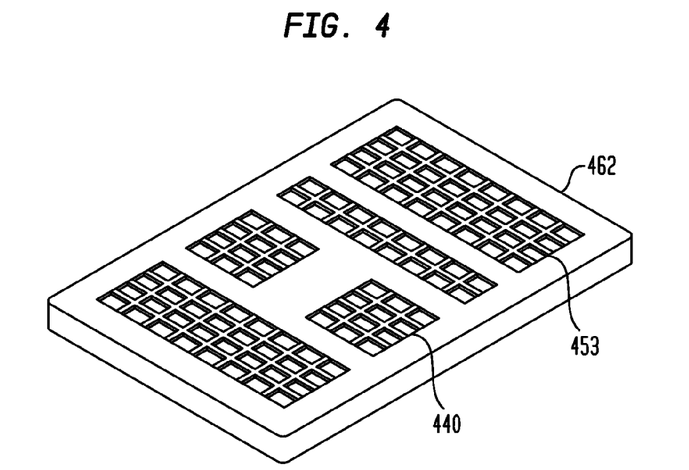
FIG. 4 is a perspective view of an implantable a universal docking station according to yet another embodiment of the present invention, in which a combination of pass-thru connectors and conversion connectors 440 are found thereon.

FIG. 4 is a perspective view of an implantable universal docking station 462 according to yet another embodiment of the present invention, in which a combination of pass-thru connectors 453 and conversion connectors 440 are found thereon. Conversion connectors 440 are connectors having one type of connector size or configuration on one side, and a different type of connector on the other side of universal docking station 462, such that different types of connectors are connected to universal docking station 462 and to each other, despite the differently configured connectors. Conversion connectors 440 may also be configured to provide more than a conversion in the physical dimensions or physical interface of the connectors connected thereto. For example, in one particular embodiment of the present invention, conversion connectors 440 are connected to a first connector (not shown) and receive signals from via the first connector. The received signals are processed or otherwise acted upon by one or more circuits electrically coupled to the conversion connector 440 and then output a processed signal to a second connector (not shown) coupled to universal docking station 462.

Figure 5:
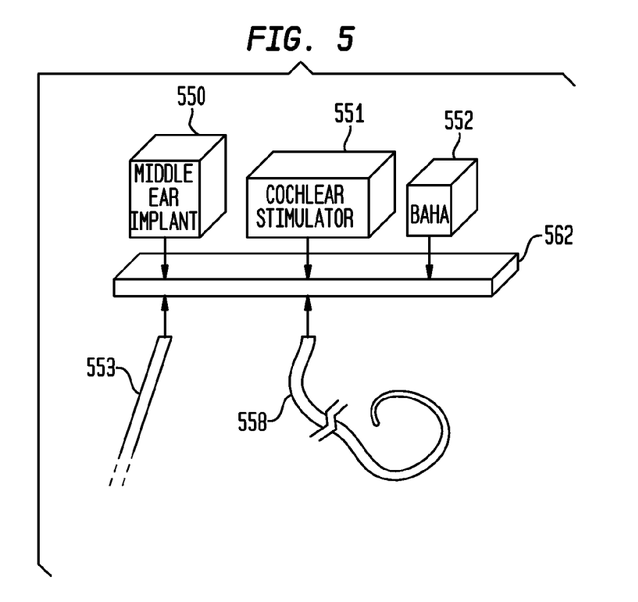
FIG. 5 is a function block diagram of various components representing a middle-ear mechanical stimulator, a cochlear stimulator, and a bone conduction transducer, according to one embodiment of the present invention.

In the embodiment of the present invention illustrated in FIG. 5, components 550, 551, and 552 represent a middle-ear mechanical stimulator, a cochlear stimulator, and a bone conduction transducer, respectively. The simplified FIGS. 4 and 5 are not depicted with securing elements, but it is to be understood that certain embodiments of the present invention will have securing elements to mount the universal docking station securely in place while others may not need securing elements in order to secure the universal docking station and other components securely in place because, for example, the recipient's tissue or other components will provide this securing element. Middle ear implant 550 is mechanically coupled to extended arm 553 such that vibration generated by middle-ear mechanical stimulator 550 is communicated via arm 553 to the recipient's hearing organs. Cochlear stimulator 551 is connected to universal docking station 562 via one of a plurality of interfaces disposed thereon, with a corresponding electrode array assembly 558 also coupled to docking station 562. Similarly, bone conduction transducer 552 is connected to docking station 562. It should be appreciated that, although various stimulators 550, 551 and 552 are illustrated in FIG. 5, the surgeon or other clinicians may have only one or a subset of the possible stimulators, or other implantable components, mounted to docking station 562. Later, additional implantable components may be added, or installed as replacements for existing components, as may be needed. For example, in one embodiment, as the recipient's hearing capability changes or degrades, different or additional stimulation components may be deemed necessary to compensate for the change or degraded ability. It is further to be understood that although a plurality of interfaces are shown for different types of implantable components, it is possible in other embodiments of the present invention that the same interface on docking station 562 may be able to receive various types of analogous or different implantable components. In one such embodiment, middle-ear mechanical stimulator 550, cochlear stimulator 551, and bone conduction transducer 552 may be connected to a single interface 453 which is appropriately configured to receive the connection. This may be due to the fact that each of those components have identical connectors. In other embodiments, this may be possible because each of those components use overlapping portions of the particular interface, even if they each do not use identical portions of the particular interface.

Figure 6A:
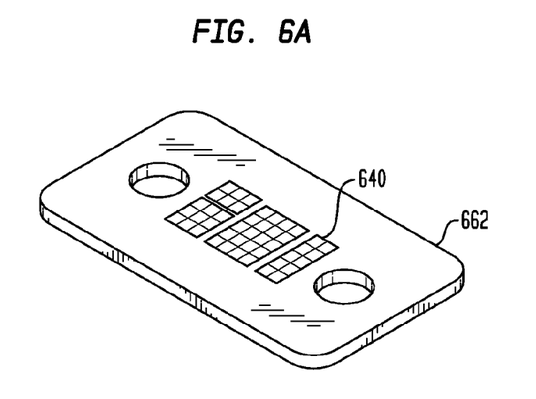
FIG. 6A is a perspective view of an implantable universal docking station according to yet another embodiment of the present invention.

FIG. 6A is a perspective view of an implantable universal docking 662 station according to yet another embodiment of the present invention. As shown, in this embodiment, universal docking station 662 has a plurality of connectors 640, illustrated in simplified form. In the particular embodiment shown, connectors 640 are basic pass-thru connectors which comprise conductors and no processors or other circuitry. In the embodiment shown, a component or cable or component-connector (all not shown) couples to one side of universal docking station 662 at connector 640, and another component or cable or component-connector (all not shown) couples to the other side of universal docking station 662 at the connector (not shown) on the flip side of universal docking station 662.

Figure 6B:
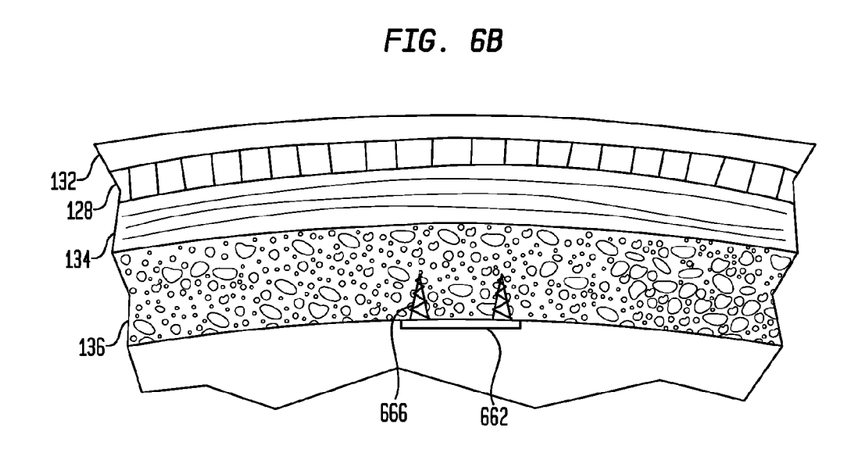
FIG. 6B is a cross-sectional view of an implantable a universal docking station according to yet another embodiment of the present invention.

For example, as shown in FIGS. 6A and 6B, in one embodiment of the present invention, a stimulation unit of a cochlear implant prosthetic hearing device might couple to connector 640 on universal docking station 662, while an electrode array (not shown) might couple to universal docking station 662 on the other side. In operation, the electrode array is further securely retained in place by its connection to universal docking station 662 which is fixed in place by a securing or fixation means such as securing element 666, shown in this embodiment in screw-type form. Also, after some period of operational use has elapsed, it may be desirable to replace or service the stimulator unit, in which case the stimulator unit can be disconnected from connector 640 of universal docking station 662. Since the electrode array is still coupled to universal docking station 662, and since universal docking station 662 is secured in place by fixation or securing elements 666, the surgically implanted position of the electrode array and other components coupled to universal docking station 662 is maintained, thus avoiding injury to the recipient while permitting simple replacement or servicing of the removed component. Alternatively, universal docking station 662 is disconnected from the electrode array such that universal docking station 662 and the stimulator unit can be removed from its surgically situated location in the recipient, such that one or both of those components can be replaced or repaired. By being able to disconnect both components while maintaining the electrode array in its surgically implanted location during the repair or replacement of those parts, it is easier and safer to provide such repairs or replacement parts than without the present invention.

Figure 7A:
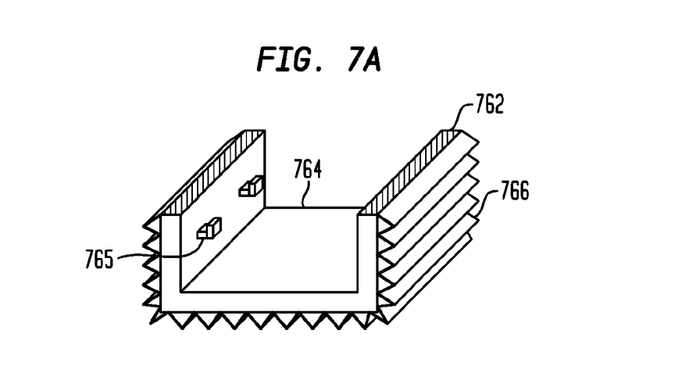
FIG. 7A is a perspective view of an implantable universal docking station according to one embodiment of the present invention.
Figure 7B:
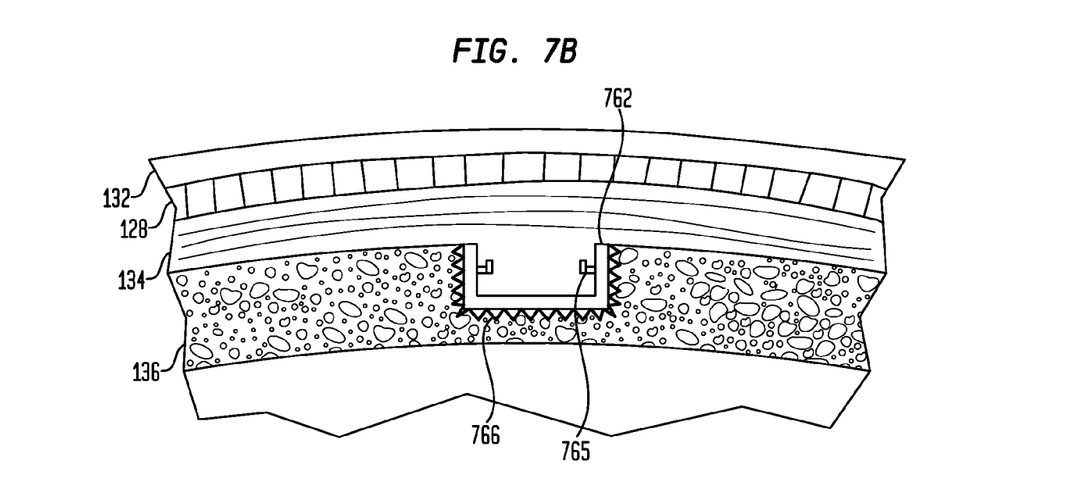
FIG. 7B is a cross-sectional view of an implantable universal docking station according to one embodiment of the present invention.

FIG. 7A is a perspective view of an implantable universal docking station according to one embodiment of the present invention. In the particular embodiment shown in FIG. 7A, universal docking station 762 comprises a compartment 764 used by components (not shown) of the prosthetic hearing device to connected to universal docking station 762. In certain embodiments, securing elements 766 are ridge shaped and are disposed on the outer surface of universal docking station 762 and configured to engage with the recipient's bone such that universal docking station 762 is held securely in place by the engagement of the recipient's bone with securing elements 766. A plurality of mechanical interfaces 765 are illustrated in FIGS. 7A and 7B. According to embodiments of the present invention, one or more implantable components (not shown in FIGS. 7A and 7B) are connected to universal docking station 762 via mechanical interfaces 765. In the embodiment illustrated in FIGS. 7A and 7B, mechanical interfaces 765 provide only a mechanical interface such that one or more implantable components are physically connected to and supported by docking station 762. It is to be understood that in other embodiments of the present invention, connection interfaces 765 may also be configured to provide an electrical connection (not shown) in addition to a mechanical connection. In such embodiments, other implantable components may be electrically coupled to docking station 762 and receive or provide electrical signals from/to the implantable components electrically connected to interface 765. Furthermore, it is to be understood that other numbers or types of securing elements 766, which may be substantially uniform or different from one another, may be provided on one or more surfaces of universal docking station 762 than is shown in FIG. 7A. In other embodiments of the present invention, securing elements 766 are configured as screw elements and are used to secure universal docking station 762 within a bed formed in the recipient's bone 136.

As shown in FIG. 7B, universal docking station 762 is implanted in the recipient's bone 136 under the recipient's skin 132, fat 128 and muscle 134 layers. Universal docking station 762 is configured to be "universal" in that various types or sizes of prosthetic hearing device components may be coupled to universal docking station 762, and that universal docking station 762 is not designed to be tied to a single or only a few designs. Rather, as long as the connecting elements of universal docking station 762 and the counterpart connecting elements of the components to be coupled to universal docking station 762 are capable of connecting to each other, and as long as the dimensions of the one or more components to be coupled to universal docking station 762 are compatible, those components are coupled to universal docking station 762. As one having skill in the art would appreciate, the "universal" nature of the universal docking station of the present invention allows for components not presently produced, designed or even conceived to be coupled to the universal docking station.

Figure 8A:
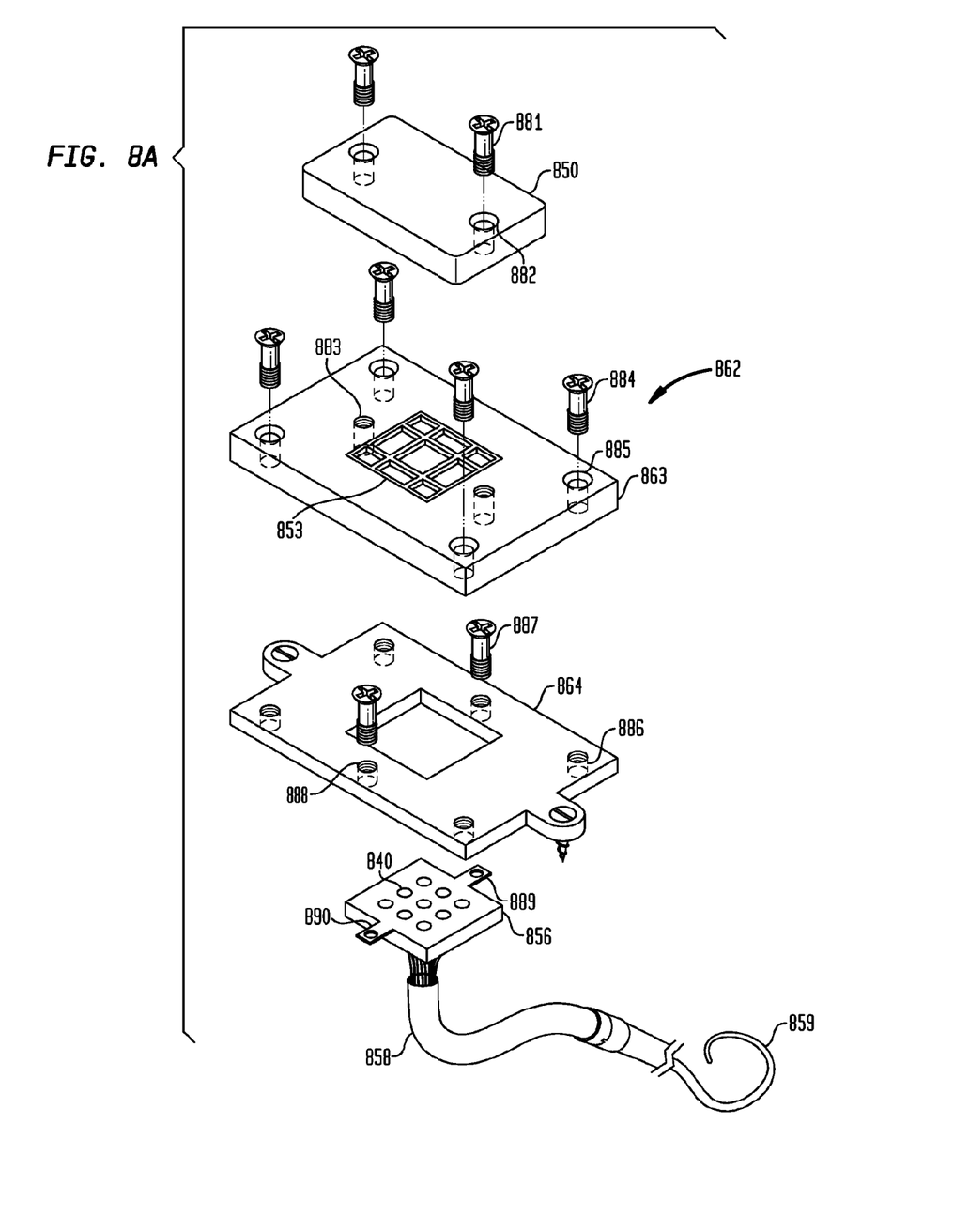
FIG. 8A is a perspective view of an implantable universal docking station comprising multiple docking station components according to yet another embodiment of the present invention.
Figure 8B:
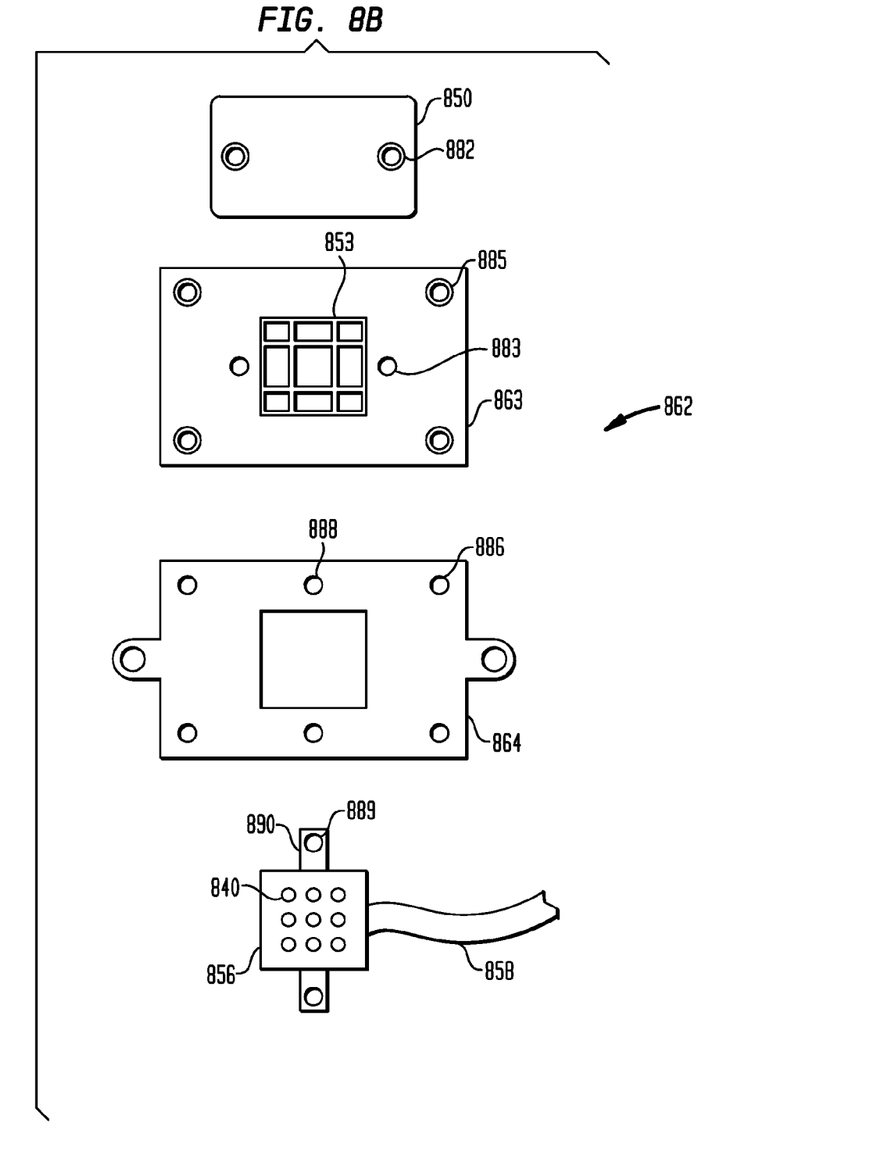
FIG. 8B is a top view of an implantable universal docking station comprising multiple docking station components according to yet another embodiment of the present invention.

FIGS. 8A and 8B is a perspective view of an implantable universal docking station 862 comprising multiple docking station components according to yet another embodiment of the present invention. In this particular embodiment, prosthetic hearing device 850 is a stimulator unit 850 of a cochlear implant system, with components retaining screws 881 configured to extend through screw access holes 882. In the illustrated embodiment, component 858 is an electrode assembly 858 having an electrode array 859 with multiple electrical contacts (not shown) configured to stimulate nerve cells (not shown) inside the recipient's cochlea 115 after the electrode array is inserted therein. Electrode assembly connector 856 comprises multiple electrical contacts 840 as well as fixation flaps 890 with threaded screw holes 889. Universal docking station 862 has a first docking station connector portion 863 which comprises connector 853, threaded screw hole 883 configured to receive component retaining screws 881 (described above), and screw access holes 885 through which connector retaining screws 884 extend. Universal docking station 862 further comprises a bone mounting component 864 having screw access holes 888 through which mounting component retaining screws 887 extend and into threaded screw holes 889 on fixation flaps 890 of electrode assembly connector 856, such that electrode assembly connector 856 is physically secured to bone mounting component 864. Bone mounting component 864 also comprises threaded screw holes 886 which receive connector retaining screws 884 in order to physically secure docking station connector portion 863 to bone mounting component 864.

In operation, the particular embodiment of the present invention illustrated in FIGS. 8A and 8B allows for decoupling different parts, from one to all of the parts illustrated in FIGS. 8A and 8B, depending on the particular part or component needing to be replaced or repaired. For example, where only stimulator unit 850 needs to be replaced, screws 881 are removed and stimulator unit 850 decoupled from the rest of universal docking station 862 and its docking station connector portion 863, bone mounting component 864 and electrode assembly 858 remaining securely in place while stimulator unit 850 is removed and replaced.

Where docking station connector unit 850 is being replaced, for example where technological advances allows for an improved connector which provides improved quality, efficiency, power consumption, signal strength, among others, connector unit 850 is decoupled from bone mounting component 864 and stimulator unit 850 and replaced. During the described replacement of docking station connector unit 850, bone mounting component 864 and electrode assembly 858 mounted thereto remains securely mounted in place, thus ensuring that the position of electrode array 859 does not change its position or orientation with respect to the nerves.

Where even bone mounting component 864 needs to be replaced, for example where a bone mounting component 864 having a different window or port is to be provided to accommodate an enlarged or differently shaped window or port, it can be decoupled from electrode assembly 858 and its electrode assembly connector 856, and then from docking station connector unit 850 in order for it to be replaced.

Although universal docking station 862 is depicted and illustrated in FIGS. 8A and 8B as having various threaded screw holes 883, 886 and 889 as well as screw access holes 882, 885, and 888, it is to be understood that other configurations of the threaded screw holes and screw access holes are used with the present invention, as well as securing means other than screws and threaded holes. For example, the various components are clipped, tab-retained, compression fit, and may otherwise be secured using various securing schemes and associated components and parts. Furthermore, referring to the particular embodiment described above and illustrated in FIGS. 8A and 8B, it is to be understood that the same screw may extend through multiple components. For example, one or more screws each may extend through stimulator unit 850 and connector unit 863 via aligned screw access holes on both components and be secured to bone mounting component 864 via threaded screw holes found thereon.

Figure 9:
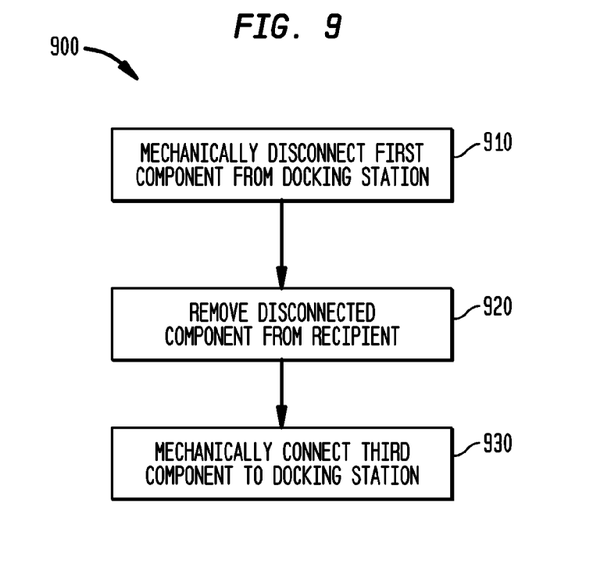
FIG. 9 is a flowchart illustrating a method for upgrading an implantable prosthetic hearing device according to one embodiment of the present invention.

FIG. 9 is a flowchart illustrating a method 900 for upgrading an implantable prosthetic hearing device according to one embodiment of the present invention. In block 910, a first implantable component is mechanically disconnected from the universal docking station. In block 920, the disconnected first component is removed from the recipient. In block 930, a third component is mechanically connected to the universal docking station in the recipient. In other embodiments of the present invention, the mechanical connection further comprises an electrical connection such that implantable components mechanically and electrically connected to the docking station may provide electrical signals for further processing by other components implanted within the recipient.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A system for implantation in a recipient, the system comprising:
    first and second functional implantable components configured to interoperate in order to stimulate the recipient's ear; and
    an implantable docking station having a plurality of interfaces comprising:
        a first interface configured to at least one of detachably mechanically and electrically connect to said first component; and
        at least a second interface configured to at least one of detachably mechanically and electrically connect to said second component, wherein:
        one of said plurality of interfaces is configured to at least one of detachably mechanically and electrically connect to a third component; and
        said third component is configured to perform an analogous function as one of said first and second components.

2. The system of claim 1, wherein said first component is a middle ear mechanical stimulator, and wherein said third component is a cochlear implant electrode assembly.

3. The system of claim 1, wherein said first component is a mechanical output transducer for a bone conduction device, and wherein said third component is a cochlear implant electrode assembly.

4. The system of claim 1, wherein said first component first component is a middle ear mechanical stimulator, said second component is a mechanical output transducer for a bone conduction device, and wherein said third component comprises a cochlear implant electrode assembly.

5. The system of claim 1, wherein said first component is detached from said first interface, and wherein said one of said plurality of interfaces configured to mechanically connect to said third component is said first interface.

6. The system of claim 1, wherein said plurality of interfaces comprises a third interface to at least one of detachably mechanically and electrically connect to said third component.

7. The system of claim 1, further comprising:
    one or more retention elements disposed along an outer surface of said implantable docking station and configured to securely retain said docking station in the recipient.

8. The system of claim 7, wherein said one or more retention elements is configured to provide a compression fit in an implantation site in the recipient's bone.

9. The system of claim 1, wherein said implantable docking station further comprises at least one electronic circuit disposed therein, said electronic circuit configured to communicably couple to at least one of said first, second and third functional components.

10. A method for upgrading an implanted system comprising an implanted docking station having a plurality of interfaces, a first one of said interfaces at least one of detachably mechanically and electrically connected to a first functional implantable component, and a second one of said interfaces at least one of detachably mechanically and electrically connected to a second implantable component, the method comprising:
    disconnecting said first component from said first interface of the implanted docking station;
    removing said disconnected first component from the recipient; and
    at least one of detachably mechanically and electrically connecting a third component having an analogous function as said first component to one of said plurality of interfaces.

11. The method of claim 10, wherein connecting said third component to one of said plurality of interfaces comprises:
    at least one of detachably mechanically and electrically connecting said third component to said first one of said interfaces.

12. The method of claim 10, wherein said plurality of interfaces comprises a third interface and wherein connecting said third component to one of said plurality of interfaces comprises:
    at least one of detachably mechanically and electrically connecting said third component to said third interface.

13. The method of claim 10, wherein said first and second functional components are configured to interoperate in order to stimulate the recipient's ear, and wherein said first component comprises a middle ear mechanical stimulator and wherein said third component comprise a cochlear implant electrode assembly.

14. The method of claim 10, wherein said first and second functional components are configured to interoperate in order to stimulate the recipient's ear, and wherein said first component comprises a mechanical output transducer for a bone conduction device, and wherein said third component comprise a cochlear implant electrode assembly.

15. The method of claim 10, wherein:
    said first and second functional components are configured to interoperate in order to stimulate the recipient's ear;
    said first component comprises a mechanical output transducer for a bone conduction device;
    said second component comprises a middle ear mechanical stimulator; and
    said third component comprise a cochlear implant electrode assembly.

16. An implantable docking station having a plurality of interfaces comprising:
    a first interface configured to at least one of detachably mechanically and electrically connect to a first functional implantable component; and at least a second interface configured to at least one of detachably mechanically and electrically connect to a second functional component, wherein:

said first and second functional implantable components are configured to interoperate in order to stimulate the recipient's ear one of said plurality of interfaces is configured to at least one of detachably mechanically and electrically connect to a third component; and said third component is configured to perform an analogous function as one of said first and second components.

17. The implantable docking station of claim 16, wherein said first component is a middle ear mechanical stimulator, and wherein said third component is a cochlear implant electrode assembly.

18. The implantable docking station of claim 16, wherein said first component is a mechanical output transducer for a bone conduction device, and wherein said third component is a cochlear implant electrode assembly.

19. The implantable docking station of claim 16, wherein said first component first component is a middle ear mechanical stimulator, said second component is a mechanical output transducer for a bone conduction device, and wherein said third component comprises a cochlear implant electrode assembly.

20. The implantable docking station of claim 16, wherein said first component is detached from said first interface, and wherein said one of said plurality of interfaces configured to mechanically connect to said third component is said first interface.

21. The implantable docking station of claim 16, wherein said plurality of interfaces comprises a third interface to at least one of detachably mechanically and electrically connect to said third component.

22. The implantable docking station of claim 16, further comprising:

one or more retention elements disposed along an outer surface of said implantable docking station and configured to securely retain said docking station in the recipient.

23. The implantable docking station of claim 22, wherein said one or more retention elements is configured to provide a compression fit in an implantation site in the recipient's bone.

24. The implantable docking station of claim 16, wherein said implantable docking station further comprises at least one electronic circuit disposed therein, said electronic circuit configured to communicably couple to at least one of said first, second and third functional components.

* * * * *